United States Patent
Jordan et al.

(10) Patent No.: US 6,774,124 B2
(45) Date of Patent: Aug. 10, 2004

(54) CHELATED 8-HYDROXYQUINOLINE AND USE THEREOF IN A METHOD OF TREATING EPITHELIAL LESIONS

(75) Inventors: Russel T. Jordan, Fort Collins, CO (US); Carl C. Hanson, Parker, CO (US); Frank S. Potestio, Parker, CO (US)

(73) Assignee: Dermex Pharmaceuticals, LLC, Fort Collins, CO (US)

(*) Notice: Subject to any disclaimer, the term of this patent is extended or adjusted under 35 U.S.C. 154(b) by 82 days.

(21) Appl. No.: 10/247,526

(22) Filed: Sep. 18, 2002

(65) Prior Publication Data

US 2003/0114484 A1 Jun. 19, 2003

Related U.S. Application Data

(60) Division of application No. 09/601,304, filed as application No. PCT/US99/02817 on Feb. 10, 1999, now Pat. No. 6,476,014, and a continuation-in-part of application No. 09/021,421, filed on Feb. 10, 1998, now abandoned.

(51) Int. Cl.[7] .................. A61K 31/555; A61K 3/147
(52) U.S. Cl. ................................. 514/187; 514/312
(58) Field of Search ........................... 514/187, 312

(56) References Cited

U.S. PATENT DOCUMENTS

| 4,401,651 | A | * | 8/1983 | Knutson | 424/78.06 |
|---|---|---|---|---|---|
| 4,877,741 | A | * | 10/1989 | Babcock et al. | 436/8 |
| 5,536,502 | A | * | 7/1996 | Mulder | 424/405 |
| 5,817,675 | A | * | 10/1998 | Whitefield | 514/312 |
| 6,124,374 | A | * | 9/2000 | Kolias et al. | 523/120 |
| 6,211,243 | B1 | * | 4/2001 | Johnson | 514/634 |
| 6,410,599 | B1 | * | 6/2002 | Johnson | 514/634 |

FOREIGN PATENT DOCUMENTS

| EP | 0506207 A2 | 9/1992 |
|---|---|---|
| EP | 0 506 207 A3 | 9/2002 |
| GB | 2 189 144 A | 4/1997 |

OTHER PUBLICATIONS

XP-002108240 Anti-proliferate Effects and Phenolypic Alternations induced by 8-hydroxyquinoline In Melanoma Cell Lines, by Jardena Nordenberg, Abraham Navogrodsky, Miriam Patla, Lina Wasserman and Abraham Warshawsky, 1990.

* cited by examiner

Primary Examiner—Vickie Kim
(74) Attorney, Agent, or Firm—Dan Cleveland, Jr.; Lathrop & Gage L.C.

(57) ABSTRACT

A chelation complex including 8-hydroxyquinoline and zinc mixed with a carrier is effective in treating the bite of the brown recluse spider.

1 Claim, 1 Drawing Sheet

CHELATED 8-HYDROXYQUINOLINE AND USE THEREOF IN A METHOD OF TREATING EPITHELIAL LESIONS

RELATED APPLICATIONS

This application is a divisional of application Ser. No. 09/601,304 filed Jan. 2, 2001 now U.S. Pat. No. 6,476,014 claiming benefit of priority to PCT/US99/02817 filed on Feb. 10, 1999 and is a continuation-in-part of application Ser. No. 09/021,421 filed Feb. 10, 1998 now abandoned.

BACKGROUND OF THE INVENTION

1. Field of the Invention

The present invention pertains to the field of oxinates and, particularly, to the therapeutic use of metal chelated 8-hydroxyquinolinates in the treatment of cancers, precancerous lesions, and other abnormal tissues.

2. Statement of the Problem

A preferred treatment modality for many cancers is surgical excision of the cancerous lesion. Surgical excision is not always desirable when surgery could sever nerves or produce scars that interfere with normal movements in tissues proximate the site of surgery.

Chemicals have been developed to treat cancers. Rate-sensitive cytotoxic drugs have cytotoxic effects on all tissue types, but are particularly effective against certain cancers that function at a metabolic rate greater than the metabolic rate of normal cells. The increased metabolic rate of these cancers makes them more susceptible to the cytotoxicity of the drugs. In this manner it is possible to provide a dosage that is fatal to cancer cells, while that same dosage is not fatal to normal cells. By way of example, U.S. Pat. No. 5,684,169 teaches the formation of cyclodextrin complexes of taxol to improve the solubility of taxol in water. Taxol is a cytotoxic drug that is believed to attack and kill cancer cells with a rate-sensitive effect.

Other chemicals are specifically designed for the treatment of skin cancers and cancers that reside close to the skin. U.S. Pat. No. 5,605,700 describes a transdermal preparation containing toremifene for use in treating cancers of the skin or cancers that reside a short distance from the skin, such as metastic lesions of breast cancer. The transdermal preparations are said to be of particular interest in the treatment of melanoma, lymphoma, Kaposi's sarcoma, and fungoides mycosis. Escharotics or caustic chemicals, such as Podophylin or tricholoroacetic acid which are used in the treatment of skin cancer, venereal warts and human papilloma virus, are designed to produce a chemical burn that destroys substantially all of the tissues in contact with the chemical. None of these chemicals is selective in destroying only the lesion while leaving behind healthy tissues that exist close to the site of the lesion, i.e., the chemicals lack selectivity and specificity.

The chemical 8-hydroxyquinoline is not used for the treatment of epithelial lesions, such as epitheliomas and venereal warts. 8-hydroxyquinoline is known by various other names including oxyquinoline, oxine, 8-hydroxychinolin, hydroxybenzopyridine, and 8-oxyquiniline. The federal government has approved 8-hydroxyquinoline for cosmetic use in low concentrations of less than five percent. At these concentrations, 8-hydroxyquinoline functions as a cosmetic biocide, as reported in JACT 11(4), 1992. U.S. Pat. No. 4,302,467 reports the use of 8-hydroxyquinoline or its chelates in combination with dehydroacetic acid or sorbic acid. The combination is reported to work synergistically against bacteria and fungus. According to the Merck Index 11th Edition, Merck & Co. publ., p. 4779. (1989), 8-hydroxyquinoline is used as a fungistat, a chelating agent in the determination of trace metals, and a disinfectant.

Chapter ten of the book Albert, Selective Toxicity 3rd Ed., New York, John Wiley & Sons, Inc. (1965) states on page 370–378 that the antibacterial action of oxine is due to chelation. Iron-chelated forms of oxine are toxic to gram-positive bacteria when mixed with $Fe^{3+}$ at a 1:1 molar ratio and a 1:2 molar ratio of oxine to iron, but toxicity diminishes at a 1:3 ratio. Despite its strong antibacteriological effects, oxine and its derivatives are not normally injected into the bloodstream because they are inactivated by red blood cells, which secrete a substance that binds oxine.

There remains a need for a topically applied therapeutic composition with selective toxicity in the treatment of epithelial lesions.

SOLUTION

The present invention overcomes the problems that are outlined above by providing a topically applied therapeutic composition having selective toxicity in the treatment of epithelial lesions. The therapeutic composition demonstrates selective toxicity on human lung cancer, breast cancer, and melanoma. Furthermore, the composition has been used to treat human patients where it demonstrates a one-hundred percent therapeutic index with selective toxicity against venereal warts, male veruoca warts, lesions produced by human papilloma virus, basal cell carcinoma, solar keratosis, and Kaposi's sarcoma. In veterinary applications where dogs, cats, and horses are the patients, the composition shows a one-hundred percent therapeutic index with selective toxicity against eye cancer, sarcoids, sarcoma, malignant melanoma, rectal adenoma, histiocytoma, and sebaceous adenoma. In this context, the therapeutic index is defined as the number of patients cured divided by the number of patients treated. While chemical excision of these lesions is accomplished, the composition is essentially without escharotic effects on healthy tissue.

A therapeutic composition according to the present invention contains 8-hydroxyquinoline or a functional homologue thereof, a metal chelating agent, and a carrier. The 8-hydroxyquinoline and the metal chelating agent are present in effective amounts for treating mammalian epithelial lesions selected from the group consisting of cancerous lesions, precancerous lesions, and warts. These mammalian epithelial lesions specifically include venereal warts, male veruoca warts, lesions produced by human papilloma virus, basal cell carcinoma, solar keratosis, Kaposi's sarcoma, eye cancer, sarcoids, sarcoma, malignant melanoma, rectal adenoma, histiocytoma, and sebaceous adenoma.

In veterinary applications, solutions according to the present invention have been used with success to treat dermal lesions including acanthosis nigricans, acne, acral lick dermatitis, allergic reactions, calcinosis circumscripta, calcinosis cutis, cutaneous asthenia, deep mycotic infection, demodicosis, acute and chronic dermatitis, dermatomycosis, eosinophillic granuloma complex, epidermal cysts, hypothyroidism, ichthyosis, insect bites, lentigo, nodular penniculitis, pemphigus, canine scabies, and thallium toxicosis. The solutions have also been used with success to treat veterinary tumors including basal cell tumors, fibroma, fibrosarcoma, granuloma, hemangioma, hemangiopericytioma, histiocytoma, intracuaneous cornyfying epithelioma, lipoma, lymphosarcoma, mast cell tumor, melanoma, papilloma, periana adenoma, reticulum cell sarcvoma, sebaceouos gland tumor, squamous cell carcinoma, sweat gland (apocrine) tumor, and transmissible venereal tumor. Injectable forms of the solutions have been used to counteract the effects of bites from the brown recluse spider, which can have disfiguring and painful consequences if left untreated.

Therapeutically effective amounts include therapeutically effective concentrations, as well as therapeutically effective ratios of the 8-hydroxyquinoline and the metal chelating agent. The preferred range for therapeutically effective ratio is one wherein the molar ratio of 8-hydroxyquinoline to the metal chelating agent ranges from 1:1 up to 1:N, where N is the oxidation state of the metal chelating agent. At the ratio of 1:N, the chelated oxine is easily transported across the cell membrane because it has a neutral charge. Charged species are also observed to be thrrapeutically effective. Where the metal has a valence of +2, therapeutically effective ratios range from 1:1 to 1:3, and the most preferred ratio is about 1:2. The 8-hydroxyquinoline is preferably present in an amount ranging from five percent to twenty percent of the composition by weight, and the most preferred amount of 8-hydroxyquinoline is about ten percent by weight. More or less 8-hydroxyquinoline may be used. For example, injectable forms or orally consumed forms may have reduced concentrations for long term uses, such as one half percent to five percent concentrations of chelated 8-hydroxyquinoline to be used as continuing maintenance treatments for a cancer patient who is in remission but remains at risk for a recurrence of cancer. The amount of 8-hydroxyquinoline may be increased beyond about twenty percent by weight, but these higher concentrations, in combination with zinc chloride chelating agent, are likely to induce a sensitized reaction in the patient. Use of these higher concentrations may be justified when faced with a tumor or lesion that is particularly difficult to remove.

As stated above, the therapeutic compositions include a metal chelating agent. This agent is preferably a chelatable metal bonded to a halogen, which yields an ionic species of the metal in solution. This reaction is free for covalent and coordinate bonding with oxine in solution. The metal is preferably a heavy metal or a transition metal. Heavy metals are more preferred, and the preferred heavy metals are copper, iron, manganese, molybdenum, and cobalt. Zinc is the most preferred heavy metal. The metal is preferably provided as a salt including a metal and a halogen, thought he halogen is not required for purposes of the invention. Chlorine is the most preferred halogen. Thus, the most preferred metal chelating agent is provided as zinc chloride.

The carrier is preferably formed of a gel base to enhance the time during which the composition is retained on the epithelial lesion where it is applied. Lecithin is preferably added as a penetrating agent, and the penetrating effect of lecithin may be enhanced by the use of dimethyl sulfoxide (DMSO). The carrier also contains an emollient, such as isopropyl palmitate or isopropyl myristate. The gel base is made of a hydrophilic polymer, such as polyacrylamide or polyoxyalkylene derivatives of propylene glycol. A topical steroid, such as 1–2% hydrocortizone may be added to decrease the incidence or severity of contact dermatitis proximate the site of topical application. Humectants, such as propylene glycol may be added to reduce dryness of the lesion during the course of treatment.

A further preferred aspect of the invention is the use of antioxidants to stabilize chelated 8-hydroxyquinoline in vivo. Nordihydroguiaretic acid, derivatives of nordihydroguiaretic acid, and functional homologues of nordihydroguiaretic acid stabilize zinc-chelated 8-hydroxyquinoline against inactivation by thermolabile substances in the blood for solutions that are injected into the body. Similarly, 8-hydroxyquinoline and zinc chloride coprecipitated with sodium ascorbate forms a stable orally administrable product having therapeutic efficacy.

The composition is administered to the epithelial lesion by topical application, injection, or oral administration. Where the lesion is scarred or thickening is observed, topical efficacy is enhanced by scraping and perforating the lesion with a needle or scalpel prior to topical application of the ointment, in order to enhance the penetration of the ointment into the lesion. Only one topical application is typically required, and the tissue forming the lesion is expected to turn black and necrotic after about two to four weeks. The dead tissue is peeled away, and the wound site typically heals to completion after another three to four weeks have passed. Even where large lesions have been removed in this manner, there is typically no scarring, and even the hair follicles are restored to full function. Additional amounts of ointment may be applied if tumor necrosis is not proceeding quickly enough. Additional solution is preferably applied to the wound margins after the removal of necrotic tissue to assure that all of the cancer cells have been eliminated.

DETAILED DESCRIPTION OF THE PREFERRED EMBODIMENT

Figure 1:
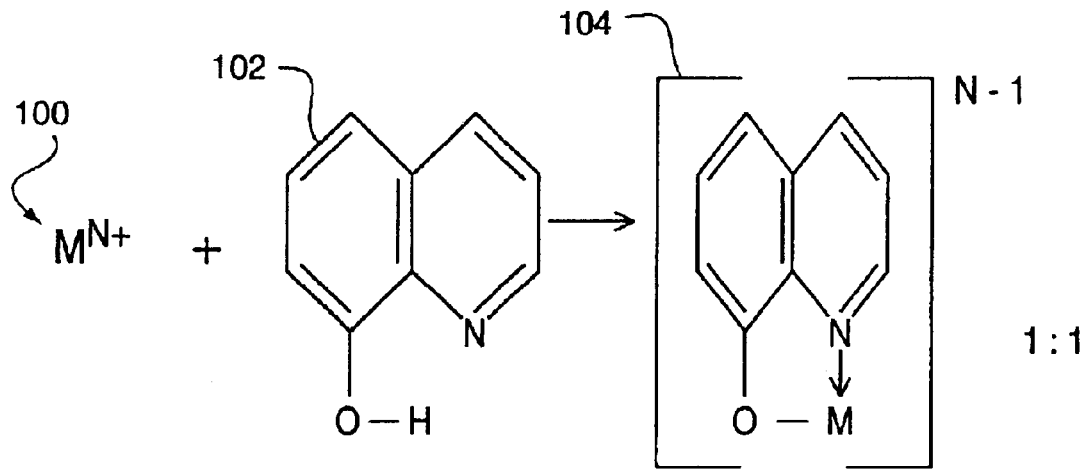
FIG. 1 depicts the chelation mechanism between a metal and oxine.
Figure 1:
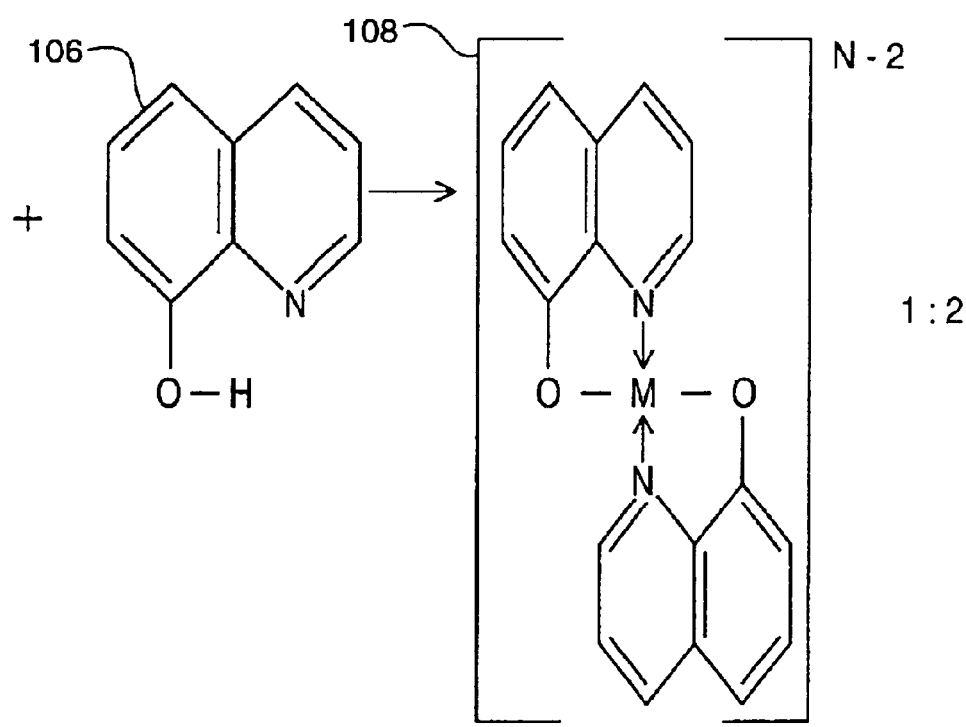

FIG. 1 depicts the chelation mechanism for 8-hydroxyquinoline. A metal chelating agent M 100 has an oxidation state of N+. The metal chelating agent M 100 reacts with 8-hydroxyquinoline 104 to produce a 1:1 metal oxinate 104 having a valence of N−1. A second 8-hydroxyquinoline molecule 106 reacts with the 1:1 metal oxinate 104 to produce a 1:2 metal oxinate 108. This process is repeated N times until the resultant oxinate has a neutral charge. even then there is coordinate attraction between the metal M 100 and the heterocyclic nitrogen atoms in other oxinates. The lowest ratio oxinates, e.g., the 1:1 oxinate 104, are the most stable products due to the steric hindrance that the large oxinate ligands provide as the reaction proceeds. Thus, if the reaction is limited by the 8-hydroxyquinoline reagent, the lower ratio species will predominate. Oxine has a high avidity for metals, and the reaction goes to substantial completion.

Ionic reaction products, i.e, those having a ratio less than 1:N, are subjected to partition effects where cell membranes regulate the intake of cations. On the other hand, uncharged complexes are liposoluble, and readily penetrate cell membranes in a manner in which the cell cannot regulate. While 8-hydroxyquinoline is normally not toxic, chelated forms of 8-hydroxyquinoline do have cytotoxic effects in mammalian cells. This cytotoxic effect is empirically observed for both the charged and uncharged reaction products.

A general theory of pharmacokinetics in the invention is that abnormal mammalian epithelial cells have membranes which are more permeable to chelated forms of 8-hydroxyquinoline than are normal cell membranes. Thus, the chelated 8-hydroxyquinoline is transported across abnormal cell membranes in a greater concentration than is permitted by normal cell membranes. It follows that topically applied, orally administered or injected forms of chelated 8-hydroxyquinoline have a greater cytotoxic effect upon the abnormal cells because abnormal cells absorb it in a greater concentration. This theory accounts for the observed selective toxicity to epidermal lesions and cancerous tumors. It does not necessarily matter whether the cytotoxicity inside the cell derives from the metal chelating agent or the 8-hydroxyquinoline, but one theory of operation explaining the observed cytotoxicity is that the oxyquinoline is the transport agent and the metal chelating agent, preferably, a heavy metal chelating agent, is primarily responsible for the observed cytotoxicity inside the cell. Thus, it is possible to increase the selective or specific cytotoxic effects of the chelated compound by increasing the toxicity of the heavy metal, e.g., by selecting osmium or arsenic. The metal may also be a radioactive isotope having a short half life of a few days or hours, such as $^{28}Mg$, $^{198}Au$, and $^{52}Fe$.

In addition to topical applications of the compositions, nordihydroguiaretic acid is used to stabilize the chelated 8-hydroxyquinoline in solutions that are injected into the patient. Nordihydroguiaretic acid is an antioxidant that protects the chelated oxine compositions against inactivation that, otherwise, might occur due to secretions from the blood that tend to inactivate oxine. Similarly, another antioxidant, sodium ascorbate, is coprecipitated with oxine and zinc chloride from a solution of ethanol and water to form an orally administrable product, which also has in vivo utility.

Patients sometimes report a burning sensation at the lesion after topical application of the chelated oxinates. Therefore, it is preferred to place an emollient into the composition, in order to sooth the burning sensation. Penetrating agents, such as lecithin or DMSO, enhance the efficacy of the compositions.

The following working examples set forth preferred methods and materials for use in practicing the invention.

EXAMPLE 1

Preparation of a Zinc-Chelated Liquid Solution of 8-Hydroxyquinoline for Use in Treating Epithelial Lesions Bulk stock solutions were made for later use as intermediates in mixing the final solution. The bulk stock solutions included a gel base solution that was used to stabilize the final product and impart a suitable thickness for the intended environment of use. A lecithin/isopropyl palmitate solution was also prepared.

The gel base solution was prepared by mixing 20 grams (gm) of Pluronic F127™[1] with 0.2 gm potassium sorbate. Purified water was added to bring the total volume to 100 ml. Pluronic F127™[1] is a high molecular weight polyoxyalkylene ether derivative of propylene glycol having water soluble, surface active, and wetting properties. The ingredients were mixed in a Braun mixer, sealed in a bowl, and stored under refrigeration at about 5° C. once all of the granules became wet. The solution was refrigerated to avoid solidification of the gel, which occurs at room temperature.

[1] Pluronic F127 is a trademark of the BASF Corporation located in Parisippany, N.J.

The lecithin/isopropyl palmitate solution was prepared by dispersing 100 gm of granular soya lecithin and 0.66 gm of sorbic acid in isopropyl palmitate (100 gm or 117 ml). The dispersed mixture was allowed to stand overnight at room temperature of about 20° C. A liquid formed having a syrup-like consistency.

A 100 gm aliquot of the gel base solution was mixed with 22 ml of the lecithin/isopropyl palmitate solution and 10 ml of distilled water. The mixture was stirred to visual homogeneity. Ten gm of 8-hydroxyquinoline and 20 gm of $ZnCl_2$ were added to the mixture, which was again stirred to homogeneity.

EXAMPLE 2

Topical Application of a Zinc-Chelated 8-Hydroxyquinoline Solution to Cure Athymic Nude Mice of Cancerous Lesions Corresponding to Explanted Samples of Human Lung Cancer A live human lung cancer cell line Calu-1 or SW-900, as reported by Fogh, J., et al. 59 J. Natl. Cancer Inst. 221–225 (1977), is an epidural lung cancer having an undifferentiated in vitro cytopathology. Cell lines of this type are known to grow tumors of corresponding cytopathology when explanted into athymic nude mice, as reported by Fogh and Giovanella eds., *The Nude Mouse in Experimental and Clinical Research*, Academic Press, London, pp 235–266 (1978) (see especially p. 239). Athymic nude mice may be purchased from specially maintained breeding colonies throughout the United States, such as the breeding colony at the University of Nevada in Reno, Nev. Athymic nude mice are especially desirable to test the efficacy of anticancer compositions because athymic mice lack immune systems. Thus, the mice do not have immune systems to attack explanted cancers in the mice, and the efficacy of anticancer compositions upon such cancers is primarily due to the compositions alone.

The test procedures that are outlined below are substantially the same as procedures that have actually been performed on athymic nude mice. The procedures below have been modified slightly to present the most preferred mode of performing the procedures.

One hundred and fifty athymic nude mice are obtained from a reputable supplier, e.g., the breeding colony at the Worchester Institute, in Worchester, Mass. The mice are split into a treatment test population of fifty mice, a no treatment test population of fifty mice, and a control population of fifty mice. The populations are maintained as separate groups using conventional procedures for maintaining breeding colonies of athymic nude mice under sterile conditions.

A human epithelial lung cancer cell line, e.g., the Calu-1, SW-900, or MX-1 lung adenocarcinoma line, is cultured in a suitable growth medium, e.g., 50 ml of Eagle's MEM medium (purchased from Life Technologies, Inc., Gaithersburg, Md.), which is supplemented with 10% fetal calf serum and 50 µg/ml gentamicin from Sigma Chemical Co. of St. Louis, Mo. The cells are maintained in a 5% humidified $CO_2$ atmosphere at 37° C. in 75 $cm^2$ plastic tissue culture flasks, with media passage at 5–7 day intervals.

A sample of approximately five million cancer cells is taken by 20 gauge trocar and extruded into the subcutaneous tissue at the posterior base of the neck on an athymic nude mouse. The procedure is repeated for each member of the treatment and no treatment test populations. Conventional sterile procedures are used while working with the mice to avoid infecting the mice with pathogens other than the cancer cell line. Live tissue from surgical patients having human lung cancer may be substituted for the cultured cell lines.

Approximately one-hundred percent of the mice can be expected to survive the grafting procedure. If proper explantation procedures are used, as will be understood by those who are skilled in those procedures, approximately one-hundred percent of the explanted cancer cells will produce epithelial lesions proximate the site of trocar insertion into the mouse. The explanted cancer is permitted to grow for approximately two to three weeks until a cancerous epithelial lesion of approximately 1.5 to 2 cm in diameter is externally visible.

The untreated test population will typically die within sixty days. Once deaths begin occurring, which is usually within about thirty days, it is preferred to euthanize the entire untreated test population to prevent unnecessary suffering. The deaths typically occur from strangulation due to growth of the cancerous tumor at the base of the neck.

The topical solution that was produced in Example 1 is removed from refrigerated storage and stirred to substantial homogeneity. A cotton swab is dipped into the solution. An athymic nude mouse having a posterior neck lesion approximately 1.5 to 2 cm in diameter is selected from the treatment test population. A needle is used to perforate the epidermal portion of the lesion at locations spaced about one millimeter apart from one another. A swab is used to apply a coating of solution over the entire lesion and extending at least one-half cm beyond the visible margins of the lesion. This procedure is repeated for each member of the treatment test population. A single topical application of the solution is the sole and exclusive time that the solution is applied to the lesions.

The treatment test population is monitored for nine months after topical application of the solution. Notes are taken as to the progress of cancer in the mice. The lesions appear inflamed on the first day after topical application. Three to five days after topical application, the lesions appear black with white streaks on the surface. Eight to ten days after the topical application, the lesions appear black and necrotic. Fourteen to sixteen days after the topical application, the lesions have sloughed off. Pathologic examination of tissue samples taken from ten individual mice at the interior margins of the sloughed lesion confirms that no cancer is visibly apparent at the margins. In thee to four weeks after topical application, the tissue at the former lesion sites has healed to become substantially indistinguishable from normal tissue with no evidence of scarring. The treatment test population exhibits cachexia or a slight emaciation corresponding to an average weight of about 4 to 5 gm less than the control population.

The treatment test population mice and the control population mice are monitored for nine months after topical application of the solution. One-hundred percent of the treatment test population typically survives the procedure with no evidence of cancer after nine months, i.e., the therapeutic index of the solution approximates one hundred percent. This success is contrasted against a one hundred percent mortality in the untreated test population, if the untreated test population has not been euthanized to prevent unwarranted suffering.

EXAMPLE 3

Topical Application of a Zinc-Chelated 8-Hydroxyquinoline Solution to Cure Athymic Nude Mice of Cancerous Lesions Corresponding to Explanted Samples of Other Human Cancers The procedure of Example 2 is repeated for other cancers including human breast cancer, human colon cancer, and human melanoma. It is noted that lung, breast, and colon cancers are classified as malignant epithelial tumors, while melanoma is a malignant nonepithelial tumor. Thus, the study addresses both epithelial and nonepithelial tumors. Specific cell lines that may be used include SW-613 (breast duct adenoca), SW-620 (colon adenoca), and RPMI-7262 (melanoma). See, for a discussion of these cell lines, Fogh, J., et al. 59 J. Natl. Cancer Inst. 221–225 (1977), and Fogh and Giovanella eds., *The Nude Mouse in Experimental and Clinical Research*, Academic Press, London, pp 235–266 (1978) (see especially pp. 238–239).

The therapeutic index is typically one hundred percent effectiveness against all of these explanted cancers in nude mice, with one hundred percent survivorship through treatment, selectivity for the destruction of diseased tissue alone, and no apparent scarring at the former lesion site. The cancers showed no sign of recurrence in the treated test populations after nine months.

EXAMPLE 4

Preparation of Zinc-Chelated 8-Hydroxyquinoline Solutions for Injection into Athymic Nude Mice These ingredients are weighed out and combined under sterile conditions: nordihydroguiaretic acid (30 gm), 3% saline in water (30 gm), 8-hydroxyquinoline (10 gm), and $ZnCl_2$ (20 gm). The ingredients are stirred to substantial homogeneity, and stored under refrigeration at about 5° C. to provide an injectable solution.

Cruder forms of injectable solutions are provided by combining the solutions of Table 1 with forty to ninety percent by weight alcohol or normal saline solution. Isopropyl alcohol is particularly preferred for use in these solutions. Alternatively, zinc chelated oxyquinoline may be mixed directly with alcohol to make a crude injectable solution.

EXAMPLE 5

Injection of Zinc-Chelated 8-Hydroxyquinoline Solution to Cure Athymic Nude Mice of Human Cancer Lesions The studies of Examples 2 and 3 are repeated in an identical manner, except the injectable nordihydroguiaretic acid solution or alcohol based solution of Example 4 is substituted for the topical solution of Example 1. In each case, a one-half ml quantity of the Example 4 solution is injected directly into subcutaneous tissue proximate the lesion.

The therapeutic index of the injected solution is typically one-hundred percent effectiveness against all of the explanted lung, breast, colon, and melanoma cancers in athymic nude mice, with one hundred percent survivorship through treatment, and no apparent scarring at the former lesion site. The cancers showed no sign of recurrence in the treated test populations after nine months. The therapeutic effects are superior with necrotic effects being observed at the lesion site approximately three days sooner than in the case of the topical ointment.

EXAMPLE 6

Various Formulations of Chelated 8-Hydroxyquinoline Solutions for Use in the Treatment of Cancerous and Precancerous Epithelial Lesions Table 1 below shows various topical product formulations that may be used to dispense therapeutically effective amounts of 8-hydroxyquinoline and zinc chloride. In Table 1 below, "NDGA" represents nordihydroguiaretic acid. "P20%" represents a solution that contains 20% Pluronic 127 NF[1] by weight, in addition to 0.2% potassium sorbate, and 79.8% distilled water. "P30%" represents a solution that contains 30% Pluronic 127 NF™[1] by weight, in addition to 0.2% potassium sorbate, and 69.8% distilled water. "P40%" represents a solution that contains 40% Pluronic 127 NF[1] by weight, in addition to 0.2% potassium sorbate, and 59.8% distilled water. "Lec/Is" refers to a solution that contains 100 gm granular soya lecithin, 100 gm isopropyl palmitate, and 0.66 gm sorbic acid.

Examples of these gel bases include Aquabase™[2], which is a hydrophilic combination of petrolatum, mineral oil, mineral wax, woolwax, alcohol and cholesterol, and Plastibase 50-W™[3].

[2] Aquabase is a trademark of the Paddock Laboratories located in Minneapolis, Minn.
[3] Plastibase W-50 is a registered trademark of E. R. Squibb & Sons located in Princeton, N.J.

TABLE 1

TOPICAL OINTMENT PRODUCT FORMULATIONS

| Sample | 8-Hydroxy-quinoline (gm) | Zinc Chloride (gm) | Distilled Water (ml) | NDGA (gm) | P20% (q.s. gm) | P30% (q.s. gm) | P40% (q.s. gm) | Aquabase (q.s gm) | Plastibase (q.s gm) | Quercetin (gm) | Larrea (gm) | Lec/ls (ml) | DMSO (ml) | $Sb_2S_3$ (gm) | Methyl Cellulose (gm) |
|---|---|---|---|---|---|---|---|---|---|---|---|---|---|---|---|
| A | — | 60 | 30 | — | — | — | — | — | — | — | — | — | — | 40 | — |
| B | 10 | 20 | 10 | — | 100 | — | — | — | — | — | — | 22 | — | — | — |
| C | 10 | 20 | 10 | — | — | — | 100 | — | — | — | — | 22 | — | — | — |
| D | 10 | 20 | 10 | — | 100 | — | — | — | — | — | — | 20 | — | — | 2 |
| E | 10 | 20 | 10 | 10 | 100 | — | — | — | — | — | — | 18 | — | — | — |
| F | — | 10 | 10 | 10 | 100 | — | — | — | — | 10 | — | 18 | — | — | — |
| G | 10 | 20 | 10 | — | 100 | — | — | — | — | — | — | 15 | — | — | — |
| H | 10 | 20 | 10 | — | 100 | — | — | — | — | — | — | 15 | — | — | 2 |
| I | 10 | 20 | 10 | — | — | 100 | — | — | — | — | — | 18 | — | — | — |
| J | 10 | 20 | 15 | — | — | — | — | 100 | — | — | — | 20 | — | — | — |
| K | 10 | 40 | 10 | — | — | — | — | 100 | — | 10 | — | — | 5 | — | — |
| L | 10 | 40 | 10 | — | — | — | — | 100 | — | — | 10 | — | 10 | — | — |
| M | 10 | 4 | 15 | — | — | — | 100 | — | — | — | — | 15 | — | — | — |
| N | 10 | 20 | 10 | — | — | — | 100 | — | — | — | — | 22 | — | — | — |
| O | 10 | 40 | 8 | — | — | — | — | 100 | — | — | 10 | — | 5 | — | — |
| P | 10 | 40 | 10 | — | — | — | — | 100 | — | — | 10 | — | — | — | — |
| Q | 10 | 40 | 10 | — | — | — | — | 100 | — | — | 10 | — | 5 | — | — |
| R | 10 | 40 | 10 | — | — | — | — | 100 | — | — | — | — | 10 | — | — |
| S | 10 | 40 | 20 | — | — | — | — | 100 | — | — | — | — | — | — | — |
| T | 10 | 40 | 20 | — | — | — | — | 100 | — | — | — | — | — | — | — |
| U | 10 | 20 | — | — | — | 100 | — | — | — | — | — | 18 | 10 | — | — |
| V | 10 | 40 | 20 | — | — | — | — | 100 | — | — | — | 20 | — | — | — |
| W | 0 | 20 | 10 | — | 100 | — | — | — | — | — | — | 10 | 18 | — | — |
| X | — | 67.5 | 35 | 13.75 | — | — | — | — | — | 17.5 | — | — | — | — | — |

[1] Pluronic F127 is a trademark of the BASF Corporation located in Parisippany, N.J.

The Pluronic 127 NF[1] solutions have pharmacoactivity that facilitates the transportation of large molecules through epidermal tissues. In this manner, the gels function as an adjuvant to improve the efficacy of chelated 8-hydroxyquinoline compositions. A disadvantage of Pluronic 127 NF[1] gels is that they must be made and stored at temperatures less than 40° F. because the gels solidify at higher temperatures. Other gel bases may be used including Aquabase or other polymers dispersed in a suitable solvent for 8-hydroxyquinoline. Lecithin and other penetrants including dimethyl sulfoxide may also be used within prescribed limits to enhance the activity of the chelated oxyquinoline compositions. In Table 1, the term "q.s." is used to show that a sufficient quantity of gel was added to bring the total weight of the combined ingredients to the weight shown in the column, i.e., 100 gm.

[1] Pluronic F127 is a trademark of the BASF Corporation located in Parisippany, N.J.

Other commercially available gel bases are also useful when used according to the manufacturer's instructions.

EXAMPLE 7

Use of Zinc-Chelated 8-Hydroxyquinoline Solutions to Treat Lesions in Humans

A solution corresponding to Sample B from Table 1 in Example 6 was applied topically to treat cancerous lesions, precancerous lesions, and warts on human patients. Treatment included one to three single topical applications of the ointment, and was successful in every case. A preferred treatment modality includes scraping the surface of epithelial lesions prior to application of the ointment, and this treatment is especially beneficial in the treatment of hard warts. The lesion is inspected about two days after treatment. Additional ointment is applied about one week after the first application if necrosis of the lesion is not apparent. In approximately one to two weeks time, the necrotic lesion tissue is peeled away using forceps. Additional ointment is applied to the wound margins to assure elimination of cancer cells and other diseased cells. Table 2 below lists the types of lesions that were successfully treated, as well as the number of lesions that were successfully treated. The total elapsed time from the topical application to sloughing of the diseased tissue averaged approximately twelve days in each case. The patients who underwent treatment for venereal warts reported much less discomfort than normally exists for chemical removal of venereal warts.

TABLE 2

SUCCESSFUL USE OF CHELATED 8-HYDROXYQUINOLINE IN HUMANS

| Lesion Type | Number of Lesions | Location |
| --- | --- | --- |
| Basal cell | 2 | Left side of nose |
|  | 1 | Right ear |
|  | 7 | Right forehead |
|  | 2 | Forehead |
|  | 1 | Left Cheek |
|  | 3 | Scalp |
|  | 1 | Neck |
|  | 3 | Face |
|  | 2 | Hands |
|  | 1 | Head |
|  | 2 | Left mandibular area |
|  | 1 | Arm |
|  | 2 | Left Temple |
|  | 4 | (Unspecified) |
| Solar Keratosis | 2 | Head |
|  | 1 | Right forearm |
| Human papilloma virus | 1 | Left chest |
|  | 1 | (Unspecified) |
| Venereal warts | 2 | Penis |
|  | 1 | (Unspecified) |
| Male veruoca warts | 1 | (Unspecificed) |
| Kaposi's sarcoma | 1 | Arm |
|  | 1 | Leg |
|  | 1 | Wrist |
|  | 1 | Foot |

EXAMPLE 8

Use of Zinc-Chelated 8-Hydroxyquinoline Solutions to Treat Lesions in Animals

A solution corresponding to sample B from Table 1 in Example 6 was applied topically to treat cancerous lesions and precancerous lesions on animals. Treatment was successful in every case, with the exception of one cat that died of sarcoma before the treatment was concluded. Table 3 below lists the types of lesions that were successfully treated and the type of animal on which treatment was successful.

TABLE 3

SUCCESSFUL USE OF CHELATED 8-HYDROXYQUINOLINE IN ANIMALS

| Lesion Type | Type of Animal |
| --- | --- |
| Eye cancer | 3 Cows |
| Squamous cell carcinoma | 1 Horse (Penis) |
| Sarcoid | 10 Horses; 1 Mule |
| Sarcoma | 1 Dog (leg) |
| Malignant melanoma | 2 Horses |
| Rectal adenoma | 1 Dog |
| Sebaceous gland adenoma | 1 Dog |
| Histiocytoma | 1 Dog |
| Sebaceous adenoma (two applications) | 1 Dog |
| Cutaneous Lymphoma | 1 Cat |
| Sarcoma | 2 Cats (one died before end of treatment); 1 Dog; 1 Bear |

EXAMPLE 9

Titration of Zinc-Chelated 8-Hydroxyquinoline Solution to Reduce Escharotic Effects While Optimizing Therapeutic Effect Three samples of ointment were prepared corresponding to Sample B from Table 1, except the lecithin/palmitate was not added and the weight percentage amount of zinc chloride comprised 20%, 40%, 55% and 75%, respectively, for the samples. The solutions were each applied to a population of twenty five athymic nude mice with explanted lung cancer in the manner of Example 1. The 55% and 75% samples produced substantially immediate chemical escharotic effects. The 40% sample produced heightened redness proximate the lesion site, and was therapeutically effective. At a 40% concentration, the ointment has the effect of selectively eating away the lesion before the underlying tissue has opportunity to regenerate. The 20% sample was therapeutically effective without burning, and the underlying tissue has a chance to regenerate without the formation of an eschar, i.e., the 20% solution does not tend to leave a hole at the lesion site, rather, no eschar is produced because the necrotic lesion tissue remains in place while the underlying tissue at least partially regenerates.

It is preferred not to use the Pluronic gels at high concentrations of $ZnCl_2$ because it has been observed that the gels degrade over time due to an altered solution pH.

EXAMPLE 10

Use of Zinc-Chelated 8-Hydroxyquinoline on Human Patients in a Clinical Evaluation Patient 1: A man entered a clinic to request treatment of a large growth on his right wrist. The growth was approximately eleven centimeters in diameter and circumscribed more than fifty percent of the wrist. The size and location of the growth meant that surgery would leave the man with impaired wrist movement. The growth was diagnosed as basal cell carcinoma. The surface of the carcinoma was scraped with a scalpel. A solution corresponding to Sample B of Table 1 was applied to the carcinoma using a cotton swab. The patient was subsequently monitored for two months. The patient complained of a burning sensation at the time of initial application. The growth appeared red and inflamed at its margins on the first day after treatment. One week later, the growth appeared black and necrotic. Two weeks after treatment, the growth was black and necrotic to an extent permitting the dead growth to be peeled away using forceps. A second application of solution B was made to the wound margins to assure that no cells from the excised cancer lesion has\d escaped. Pathologic examination of tissue from the wound margin confirmed that basal cell carcinoma was absent from healthy tissues at the margin of the wound. Six weeks after treatment, the wound site appeared as healthy tissue with no sign of basal cell carcinoma or scarring. Hair follicles were intact at the site of the former wound and basal cell carcinoma. The man retained full function in the affected wrist.

Patient 2: A woman entered a clinic with a basal cell carcinoma approximately one inch below the corner of her left eye. The growth was approximately one-half inch in diameter. The surgical prognosis was that removal of the growth would leave the woman with partial paralysis of the face and eye muscles. The surface of the carcinoma was scraped with a scalpel. A solution corresponding to solution B from Table 1 was applied to the carcinoma using a cotton swab. The patient was subsequently monitored for two months. The patient complained of a burning sensation at the time of initial application. The growth appeared red and inflamed at its margins on the first day after treatment. One week later, the growth appeared black and necrotic. Two weeks after treatment, the growth was black and necrotic permitting the carcinoma to be peeled away by forceps. Pathologic examination of tissue from the wound margin confirmed that basal cell carcinoma was absent from healthy tissues at the margin of the wound. Pathologic examination of tissue from the wound margin on the patient's face wrist confirmed the absence of basal cell carcinoma. Six weeks after treatment, the wound site appeared as healthy tissue with no sign of basal cell carcinoma or scarring. Hair follicles were intact at the site of the former wound and basal cell carcinoma. The woman retained full function in muscles of the face and eye.

Comparative trial: A patient had nodular pigmented lesions on his face since childhood. Three of the tumors ulcerated. Diagnosis was nevoid basal cell syndrome including multiple basal cell epitheliomas. Three of the tumors ulcerated. These were scraped and solution B from Table 1 was applied to these tumors. Necrotic tissue from the lesions was peeled away by forceps two weeks later. Ten other tumors were removed by cryosurgery. None of these tumors recurred.

A second ointment was prepared to include the ingredients of solution B, but the oxyquinoline was absent. A third ointment was prepared to include the ingredients of solution B, but zinc chloride was absent. The second and third ointments were applied to basal cell epitheliomas on the patient's face. The second and third ointments were not effective in removing the epitheliomas.

EXAMPLE 11

Veterinary Use of Zinc-Chelated 8-Hydroxyquinoline in Clinical Evaluations

Female Domestic Short Hair Cat With Allergic Dermatitis: A female cat aged six years developed a lesion approximately four inches long and two inches wide in the flank ventral region. Antibiotic and surgical treatment modalities were tried without success at three different animal clinics. The lesion recurred within a few weeks after it was surgically removed. The lesion was biopsied at the time of surgery. The histopathology report noted severe chronic (fibrotic) inflammation in the upper dermis with plentiful mature mast cells and a moderately heavy scattering of other mixed leukocytes. The epidermis had occasional shallow ulcers. A fungal stain tested negative for ringworm and surface yeasts, and no parasites were present. The diagnosis was hypersensitive or allergic dermatitis.

The zinc chelated oxyquinoline formula of Example 1 was applied to coat the lesion twice with the second application following the first application by two weeks. The lesion was scraped prior to each application. Two months and four days after the first application, the lesion had shrunk to the size of a pin head. A second biopsy confirmed the existence of allergic dermatitis in this very small region.

Female Boston Terrier With Squamous Papilloma and Sebaceous Gland Hyperplasia: An obese thirteen year old Boston terrier was diagnosed with numerous squamous papilloma tumors on the face and one tumor on the right foot. The dog's owner desired a nonsurgical treatment due to the dog's age and obesity problems. A biopsy of lip tissue showed that the epithelium was markedly hyperblastic. The underlying growth contained lobules of cystic sebaceous glands. Some melanocytes and melanin containing macrophages were observed.

Five tumors were treated by direct application to the tumor of the zinc chelated oxyquinoline formula from Example 1. Application occurred once per week, and three of the tumors were resolved after three applications. The two largest tumors included one lesion on the forehead and one on the right foot. The tumor on the right foot resolved after the fourth treatment and the largest tumor on the forehead was significantly diminished in size. Treatment was discontinued when the dog's owner temporarily moved.

Kodiak Bear With Soft Tissue Fibrosarcoma: An eight year old male Kodiak bear was diagnosed with a tumor in the dorsolateral region proximate the right carpus. The bear was anaesthetized and the tumor was biopsied. Clinical diagnosis was that of myxoid fibrosarcoma with chondroid differentiation Grade 2. There was a low to medium chance of metastasis. The tumor measured 54.5 cm at the circumference, 17 cm proximal to distal, and 21 cm lateral to base of the tumor. A diagnostic clinician noted some bone invasion and recommended amputation of the afflicted limb.

Study of the of the biopsy samples showed a moderately differentiated tumor with different lines of differentiation varying from fibrous tissue to early cartilage type tissue. Cells included spindle cells forming bundles that intersected at various angles. Myxomatous and fibrous stroma were present. Nuclei were mildly pleomorphic, oval, and had prominent nucleoli. Mitoses were occasionally present, and there were occasional giant nuclear forms. In some areas, the cells were fibrous. In other areas, the cells were plump with myxoid material or early embryonic cartilagenous type material. One area showed an anaplasia where the cells also had some giant nuclear forms and increased mitotic rates. There were no normal tissue margins.

An injectable solution was prepared by mixing ten grams of the solution Q from Table 1 with 100 grams of isopropyl alcohol. A 5 cc quantity of ten percent zinc 8-hydroxyquinoline in isopropyl alcohol was injected into the center of the tumor mass, and 3 cc were injected into each of four fingers of the tumor. The tumor was surgically removed two weeks later. Biopsy confirmed that the tumor was encapsulated at the time it was removed. No bone invasion was seen at the time that the tumor was surgically removed.

Mule With Sarcoid: An eight year old mule was diagnosed with a twelve millimeter diameter sarcoid located between the ear and the left eye. Visual diagnosis was confirmed by biopsy. The lesion was scraped and the zinc chelated oxyquinoline formula of Example 1 was applied to cover the scraped lesion. The lesion disappeared within one month. Total remission was pronounced at a followup examination two months after treatment.

Gelding With Squamous Cell Carcinoma: A twenty-one year old gelding was diagnosed with squamous cell carcinoma located on the unpigmented portions of the penis. Six lesions were present varying in diameter from five millimeters to twelve millimeters. The lesions were scraped and covered with the zinc chelated oxyquinoline formula of Example 1. Application was repeated one week later with mild swelling observed on the affected area. All lesions had completely healed at a followup examination thirty days after the second treatment.

Feline Cutaneous Lymophoma: A cat had lesions on the pad areas of all four feet. The lesions ranged in size from one half to two centimeters. Surgery to remove the lesions was impossible due to their locations and the impairment of mobility due to surgical scarring. The lesions were scraped with a scalpel and solution B from Table 1 was applied to the lesions. The lesions sloughed off and the pad areas were completely healed within about four to six weeks.

EXAMPLE 12

Preparation of Orally Administrable Compositions

A solution was mixed to include equal 33 gram weights of 8-hydroxyquinoline, sodium ascorbate, and zinc chloride in 90% ethanol with sufficient water added to just dissolve the ingredients at 110° F. The mixture stood to ambient room temperature under a ventilation hood for twenty four hours. A vacuum aspirator was used to remove remaining liquid while coprecipitating the remaining moieties from solution. The precipitate was scraped from the beaker, supplemented with 5 grams of ascorbic acid, and ground to homogeneity with mortar and pestle to yield an orally administrable composition.

An oral base may be substituted for any of the Pluronic, Aquabase, or Plastibase substances in Table 1 to provide orally administrable solutions. The oral base solutions may be applied directly to lesions of the mouth, or they may be diluted for ingestion. The oral base is made by mixing one gram of gelatin, two grams of sodium carboxymethylcellulose, one ml of isopropyl alcohol, fifty grams of Plastibase, and 500 mg of xanthan gum. Forty seven grams of distilled water are brought to a boil and added to the mixture, which stands to room temperature. Plastibase is added to the cooled mixture until a desired gel consistency is achieved.

Those skilled in the art will understand that the preferred embodiments described above may be subjected to apparent modifications without departing from the true scope and spirit of the invention. The inventors, accordingly, hereby state their intention to rely upon the Doctrine of Equivalents, in order to protect their full rights in the invention.

What is claimed is:

1. A method of treating a bite from a brown recluse spider, the method comprising the steps of:
    preparing an injectable formulation to contain:
        8-hydroxyquinoline;
        a metal chelating agent; and
        a carrier; and
    injecting the injectable formulation proximate a bite from a brown recluse spider.

* * * * *

UNITED STATES PATENT AND TRADEMARK OFFICE
CERTIFICATE OF CORRECTION

| | | |
|---|---|---|
| PATENT NO. | : 6,774,124 B2 | Page 1 of 1 |
| APPLICATION NO. | : 10/247526 | |
| DATED | : August 10, 2004 | |
| INVENTOR(S) | : Russel T. Jordan et al. | |

It is certified that error appears in the above-identified patent and that said Letters Patent is hereby corrected as shown below:

Title page, Item (60), the words "09/021,421, filed on Feb. 10, 1998, now abandoned." should read --09/021,421, filed on Feb. 10, 1998.--

Signed and Sealed this

Fifth Day of June, 2007

JON W. DUDAS
*Director of the United States Patent and Trademark Office*